(12) United States Patent
Risch et al.

(10) Patent No.: US 7,326,821 B2
(45) Date of Patent: Feb. 5, 2008

(54) REMOVAL OF OXYGENATE FROM AN OLEFIN STREAM

(75) Inventors: Michael A. Risch, Seabrook, TX (US); John Di-Yi Ou, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 569 days.

(21) Appl. No.: 10/462,351

(22) Filed: Jun. 16, 2003

(65) Prior Publication Data
US 2004/0254416 A1   Dec. 16, 2004

(51) Int. Cl.
  C07C 7/00   (2006.01)
(52) U.S. Cl. ............... 585/824; 585/639; 585/640; 585/800; 585/809; 585/820; 585/826; 95/96; 95/97; 95/98; 95/99; 95/115; 95/143; 95/144; 95/902
(58) Field of Classification Search ........... 95/96, 95/97, 98, 99, 115, 143, 144, 902; 585/639, 585/640, 800, 809, 820, 824, 826
See application file for complete search history.

(56) References Cited

U.S. PATENT DOCUMENTS

| | | | | |
|---|---|---|---|---|
| 4,079,096 A | * | 3/1978 | Givens et al. | 585/640 |
| 4,575,567 A | | 3/1986 | Vora | 568/697 |
| 6,111,162 A | * | 8/2000 | Rossini et al. | 585/824 |
| 6,118,037 A | * | 9/2000 | Piccoli et al. | 585/820 |
| 6,174,975 B1 | * | 1/2001 | Johnson et al. | 526/172 |
| 6,403,854 B1 | | 6/2002 | Miller et al. | 585/638 |
| 6,960,700 B1 | * | 11/2005 | Sethna et al. | 585/822 |

FOREIGN PATENT DOCUMENTS

| | | |
|---|---|---|
| EP | 229 994 | 7/1987 |
| JP | 272905 | 1/2000 |
| SU | 944633 | 7/1982 |

OTHER PUBLICATIONS

Tonkovich et al., "Experimental Evaluation of Designs for the Simulated Countercurrent Moving Bed Separator," AIChE Journal, vol. 42, No. 3, pp. 683-690, (1996).
Fish et al., "Design and Performance of a Simulated Countercurrent Moving-Bed Separator," AIChE Journal, vol. 39, No. 11, pp. 1783-1790, (1993).
Doelle et al., "Sorption and Catalytic Reaction in Pentasil Zeolites. Influence of Preparation and Crytal Size on Equilibria and Kinetics," Journal of Catalysis, vol. 71, pp. 27-40, (1981).
Fujino et al., "FT-IR and Quantum Chemical Studies of the Interaction between Dimethyl Ether and HZSM-5 Zeolite," J. Phys. Chem., vol. 100, pp. 11649-11653, (1996).

(Continued)

Primary Examiner—Glenn Caldarola
Assistant Examiner—Prem C. Singh (57) ABSTRACT

This invention is to a process for removing dimethyl ether from an olefin stream. The process includes contacting the olefin stream with a molecular sieve that has improved capacity to adsorb the dimethyl ether from the olefin stream. The molecular sieve used to remove the dimethyl ether has low or no activity in converting the olefin in the olefin stream to other products.

72 Claims, 1 Drawing Sheet

OTHER PUBLICATIONS

A. M. Rubishtein, "Study of the Structure and Adsorptive Properties of Hetergeneous Catalysts in the N. D. Zelinskii Organic Chemistry Institute", *Academy of Sciences of the USSR*, vol. 8, No. 55, pp. 936-951, (1967).

Saburina et al., "Adsorption of Mixtures of Dimethyl Ether and Methyl Chloride on Microporous Adsorbents," *Russian Journal of Physical Chemistry*, vol. 60, No. 12, pp. 1830-1832 (1986).

Dzhigit et al., "Heats of Adsorption of Methyl Ether and Propane on Various Cationic Forms of X Zeolite," *Russian Journal of Physical Chemistry*, vol. 42, No. 1, pp. 101-105, (1968).

Haber, Jerzy et al., "I.r. study of the transformations of olefins, alchols and ethers on zeolites", ZEOLITES, vol. 2, July, pp. 179-184 (1982).

Qiao, B., "*Removal of dimethyl ether in raffinate from MTBE extraction*", Lianyou Sheji Bianjibu Journal, 25(2), pp. 23-5 [English abstract only].

"*Infrared Spectra of Catalysts and Adsorbed Molecules—4. Dimethyl Ether in the Surface of of Alumina*," Izv Akad Nauk Sssr Ser Khim N. 10 2246-2253, Oct. 1967 [English abstract].

Saburina, E.B. et al., "*Desorption of Methyl Chloride and Dimethyl Ether from Microporous Adsorbents by an Inert Gas*", translated from Zhurnal Prikladnoi Khimii, vol. 62, No. 4, pp. 847-849, Plenum Publishing Corporation (1989).

\* cited by examiner

FIGURE

REMOVAL OF OXYGENATE FROM AN OLEFIN STREAM

FIELD OF THE INVENTION

This invention is to a process for removing oxygenate from an olefin stream. In particular, this invention is to a process for removing dimethyl ether or acetadelhyde, particularly dimethyl ether, from an olefin stream produced in an oxygenate to olefin reaction system.

BACKGROUND OF THE INVENTION

Olefins such as ethylene and propylene have a wide variety of uses. Examples include isomerization and oligomerization to fuel products, and polymerization to plastic products. In many cases, the olefins which are to be further used as a feed stream also contain contaminants such as oxygenates which must be substantially removed.

For example, U.S. Pat. No. 6,403,854 (Miller et al.) discloses removal of an oxygenate contaminant such as dimethyl ether from an olefin stream made by contacting methanol with a silicoaluminophosphate (SAPO) catalyst. The oxygenate contaminant is removed by cooling the olefin stream in a two stage quench process. In the first stage of the process, a substantial portion of the dimethyl ether is removed along with condensed water as a bottoms product. Additional dimethyl ether is removed in the second stage, and the olefin overhead is further treated for oxygenate removal by contacting with an adsorbent.

EP 0 229 994 (Union Carbide Corp.) discloses the removal of dimethyl ether from a liquid $C_3$-$C_5$ olefin. More specifically, the liquid olefin contains from 5 to 50 weight percent monoolefins having from 3 to 5 carbons, from 100 to 20,000 ppm by weight diolefins, and from 1 to 5,000 ppm by weight dimethyl ether, in liquid state through an adsorbent mass of a crystalline zeolite molecular sieve. The zeolite has a faujasite structure, and includes zeolite Y, zeolite X, and zeolite LZ-210. Preferably, the olefin stream is a mixed $C_4$-$C_5$ hydrocarbon stream and comes from a fluid catalytic cracking (FCC) unit, with the bulk of the isobutylene and/or isoamylene content in the olefin having been removed by reacting the olefin FCC product with methanol to form MTBE or TAME. The adsorption system can be a fixed bed, moving bed, simulated moving bed or fluidized bed system, but is preferably a fixed bed system.

Conventional processes for removing oxygenates such as dimethyl ether or acetaldehyde from an olefin stream are complex, provide insufficient removal of the oxygenate or convert a significant percent of the olefin product to undesirable by-products such as olefin oligomers. Therefore, additional processes are desired.

SUMMARY OF THE INVENTION

Figure 1:
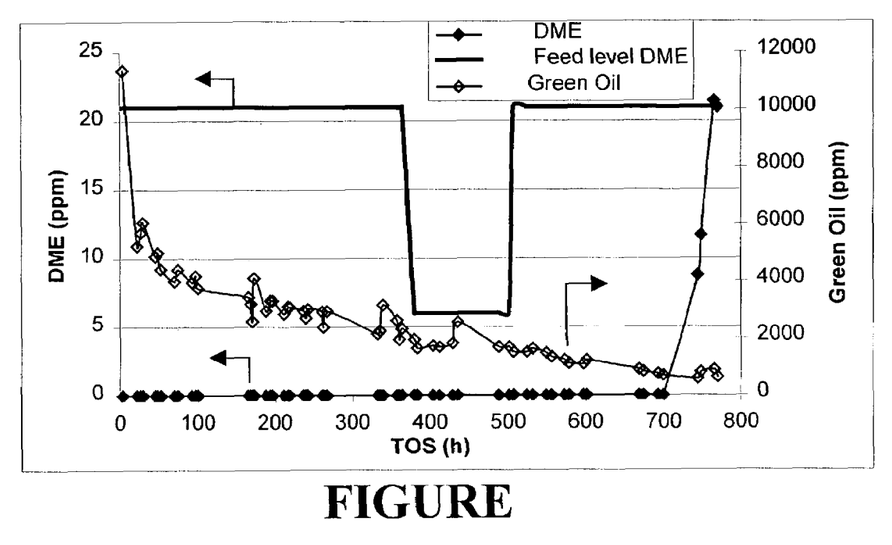
The FIGURE shows that the DME breakthrough occurs after 700 hours upon contact with the zeolite of the invention.

This invention provides a highly efficient and relatively simple process for removing oxygenate, particularly dimethyl ether or acetaldehyde, more particularly dimethyl ether, from an olefin stream. The process uses a solid adsorbent to remove a majority of the oxygenate from the olefin stream. The adsorbent can retain relatively large quantities of oxygenate, while being substantially inert to converting desired olefin product to undesirable by-product.

In one embodiment, the invention provides a process for removing oxygenate from an olefin stream, which comprises providing an olefin stream, wherein the olefin stream contains oxygenate, and a majority of the olefin stream is comprised of one or more olefins. The provided olefin stream is contacted with a solid adsorbent to remove oxygenate from the provided olefin stream. Desirably, the solid adsorbent has an oxygenate adsorption capacity of at least 0.1 wt % and a cumulative oligomer selectivity of not greater than 5 wt %. Preferably, the solid adsorbent has an oxygenate adsorption capacity of at least 0.2 wt %, more preferably an oxygenate adsorption capacity of at least 0.5 wt %, and most preferably an oxygenate adsorption capacity of at least 1.0 wt %. Also preferably, the solid adsorbent has a cumulative oligomer selectivity of not greater than 3 wt %, more preferably a cumulative oligomer selectivity of not greater than 2 wt %, and most preferably a cumulative oligomer selectivity of not greater than 1 wt %.

The contacting of the olefin stream with the solid adsorbent results in the removal of a majority of the oxygenate from the olefin stream. The oxygenate removed from the olefin stream is preferably dimethyl ether or acetaldehyde, and more preferably the oxygenate is dimethyl ether.

In one embodiment, the solid adsorbent comprises at least one ion from Group 2, 4, 6, 12, 13, 14 or 15 of the Periodic Table of the Elements. Preferably, the solid adsorbent comprises at least one ion from Group 2 or 12 of the Periodic Table of the Elements. More preferably, the solid adsorbent comprises magnesium or zinc.

In another embodiment of the invention, the provided olefin stream comprises at least 50 wt % ethylene, propylene, butylene, or a combination thereof, based on total weight of the provided olefin stream. Preferably, the provided olefin stream comprises at least 50 wt % ethylene and propylene, based on total weight of the provided olefin stream. More preferably, the provided olefin stream comprises at least 50 wt % propylene and butylene, based on total weight of the provided olefin stream.

In one embodiment, the provided olefin stream comprises not greater than 1,000 wppm oxygenate, based on total weight of the provided olefin stream. Preferably, the olefin stream comprises not greater than 1,000 wppm dimethyl ether or acetaldehyde, more preferably not greater than 1,000 wppm dimethyl ether.

Desirably, the solid adsorbent is a molecular sieve or metal oxide. Preferably, the solid adsorbent is a molecular sieve. The molecular sieve preferably has a framework structure of at least 8 rings. Also preferably, the molecular sieve is a zeolite. Particularly preferred zeolites include zeolite X, zeolite Y, ZSM-5, ZSM-11, ZSM-14, ZSM-17, ZSM-18, ZSM-20, ZSM-31, ZSM-34, ZSM-41 or ZSM-46. Of these, zeolite X or Y is preferred, with zeolite X being particularly preferred.

The solid adsorbent can be kept in continuous use by regenerating following contacting with the provided olefin stream. At least one olefin in the olefin stream that has been contacted to remove oxygenate can be polymerized to form a polyolefin.

In another embodiment of the invention, there is provided a process for removing dimethyl ether from an olefin composition made from an oxygenate. In one aspect, the process comprises contacting an oxygenate with a molecular sieve catalyst to form an olefin composition, wherein the olefin composition contains dimethyl ether. At least a portion of the olefin composition containing the dimethyl ether is contacted with the solid adsorbent of this invention to remove at least a portion of the dimethyl ether from the provided olefin stream. In another aspect, the olefin composition formed in the process is further processed to remove non-olefin components from the olefin composition prior to contacting the olefin composition with the solid adsorbent of this invention. In yet another aspect, the olefin composition formed in the process is dewatered and split into at least two olefin streams, and one of the olefin streams is contacted with the solid adsorbent of this invention.

Also provided in this invention, is a process for removing dimethyl ether from an olefin stream that contains dimethyl ether and at least 50 wt % ethylene, propylene, butylene, or a combination thereof, based on total weight of the olefin stream. The olefin stream is preferably contacted with a molecular sieve to remove at least a portion of the dimethyl ether from the provided olefin stream. The molecular sieve has a dimethyl ether adsorption capacity of at least 0.1 wt % and an oligomer accumultion of not greater than 5 wt %.

DETAILED DESCRIPTION OF THE INVENTION

I. Removing Dimethyl Ether From an Olefin Stream

This invention provides a process for removing oxygenate contaminants, for example dimethyl ether or acetaldehyde, from an olefin stream. In general, the process comprises providing an olefin stream containing an oxygenate, then removing a majority (i.e., greater than 50%) of the oxygenate present in the olefin stream.

In this invention, a solid adsorbent is used for removing the oxygenate from the olefin stream. The particular solid adsorbent has the characteristics of high oxygenate adsorption capacity and low cumulative oligomer selectivity. That is, the solid adsorbent has the ability to adsorb a substantial amount of oxygenate from the olefin stream, and is essentially inert in that it has low or no activity in converting olefins in the olefin stream to other products such as olefin dimers, oligomers or polymers (collectively referred to as oligomers). The end result in using the solid adsorbent of this invention is that the adsorbent can remove oxygenates such as dimethyl ether or acetaldehyde, particularly dimethyl ether, from an olefin stream down to a very low level. In addition, the adsorbent can hold a significant quantity of the adsorbed material, and the adsorbent does not significantly deplete the desired olefin product in the olefin stream by causing the olefin to be converted to the undesirable oligomer by-products.

II. Description of the Solid Adsorbent

The solid adsorbent of this invention is an oxygenate adsorbent that has a relatively high oxygenate adsorption capacity, yet is substantially inert to forming olefin oligomers. Oxygenate adsorption capacity, according to this invention, is defined as amount of oxygenate adsorbed (e.g., grams of oxygenate removed from olefin stream) divided by total weight of adsorbent used (e.g., grams of adsorbent used to remove oxygenate). The degree of inertness, according to this invention, is defined as cumulative oligomer selectivity, with oligomers being collectively referred to herein as olefin dimers, oligomers, and polymers. Cumulative oligomer selectivity is the amount of oligomer formed (e.g., grams of oligomer) divided by total amount of olefin contacted by the adsorbent (e.g., grams of olefin contacted with the adsorbent).

The oxygenate adsorption capacity and the cumulative oligomer selectivity is determined, according to this invention, on a continuous flow basis. Preferably, the olefin feed containing oxygenate contaminant is flowed through a vessel containing the adsorbent at a flow rate of 3 $hr^{-1}$ LHSV, a pressure of 380 psig (2721 kPa), and a temperature of 28° C., until breakthrough of the oxygenate is observed. See Examples of this application.

In one embodiment, the oxygenate adsorption capacity of the solid adsorbent used in this invention is at least 0.1 wt %. Preferably, the oxygenate adsorption capacity of this solid adsorbent of this invention is at least 0.2 wt %, more preferably at least 0.5 wt %, and most preferably at least 1.0 wt %.

In another embodiment of this invention, the cumulative oligomer selectivity of the solid adsorbent used in this invention is not greater than about 5 wt %. Preferably, the oligomer accumultion of the solid adsorbent of this invention is not greater than about 3 wt %, more preferably, not greater than about 2 wt %, and most preferably not greater than about 1 wt %. The cumulative oligomer selectivity corresponds to the amount of olefin lost from the feed stream as a result of by-product formation. The higher the cumulative oligomer selectivity, the greater the olefin feed loss.

Preferably, the solid adsorbents used in this invention are porous solids that have a relatively high surface area. In one embodiment, the solid adsorbents have a surface area of at least about 200 $m^2/g$. Preferably, the solid adsorbents have a surface area of at least about 300 $m^2/g$, more preferably at least about 400 m 2/g.

According to one aspect of this invention, the solid adsorbent comprises ions that enhance oxygenate adsorption capacity, particularly dimethyl ether or acetaldehyde adsorption capacity, more particularly dimethyl ether adsorption capacity, relative to the non-ion form of the solid adsorbent. Examples of such ions include at least one ion from Groups 2-7 and 12-16 of the Periodic Table of the Elements. The Periodic Table of the Elements referred to herein is that from CRC Handbook of Chemistry and Physics, $82^{nd}$ Edition, 2001-2002, CRC Press LLC, which is incorporated herein by reference.

The ions that are incorporated into the solid adsorbent of this invention can be present at numerous sites in or on the solid adsorbent. For example, the ions can be supported on the adsorbent, incorporated within the framework of the adsorbent, or ion-exchanged into the adsorbent. Preferred ions include at least one ion from Groups 2, 4, 6, 12, 13, 14, and 15 from the Periodic Table of the Elements; more preferably at least one ion from Groups 2 and 12. Particularly preferred non-limiting examples of oxygenate adsorption enhancing ions include zinc and magnesium.

In one embodiment of the invention, the solid adsorbent is a molecular sieve. Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., Introduction to Zeolite Science and Practice, Second Completely Revised and Expanded Edition, Volume 137, pages 1-67, Elsevier Science, B. V., Amsterdam, Netherlands (2001).

The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å.

The molecular sieves can be amorphous, crystalline, or a combination thereof. Examples include zeolite as well as non-zeolite molecular sieves, which are of the large, medium or small pore type. Non-limiting examples of these molecular sieves include the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Preferred types of molecular sieves include faujasites, pentasils, mordenite, beta, VPI, MCM, and substituted aluminophosphates such as SAPO, MeAPO, ELAPO, and ELAPSO. Non-limiting examples of the preferred molecular sieves include zeolite X, zeolite Y, VPI-5, MCM-41, ZSM-5, ZSM-11, ZSM-14, ZSM-17, ZSM-18, ZSM-20, ZSM-31, ZSM-34, ZSM-41 and ZSM-46. In one preferred embodiment, the molecular sieve of the invention is zeolite X or zeolite Y In one embodiment, the molecular sieve that is used as the solid removing agent of this invention is an ion-exchanged molecular sieve, which enhances the adsorption capacity of the molecular seive. Any conventional ion-exchange method can be used. Examples of such methods are found in Breck, *Zeolite and Molecular Sieves*, pages 529-592, John Wiley & Sons, New York (1974), and Wojciechowski and Corma, *Catalytic Cracking*, pages 68-70, Marcel Dekker, Inc., New York (1968), the descriptions of each being incorporated herein by reference. Preferred ion-exchanged molecular sieves include molecular sieves containing at least one ion from Groups 2, 4, 6, 12, 13, 14, and 15 from the Periodic Table of the Elements; more preferably at least one ion from Groups 2 and 12. Particularly preferred ions include zinc and magnesium.

In another embodiment of the invention, the solid adsorbent is a metal oxide adsorbent. The metal oxide adsorbent can be amorphous, crystalline or a combination thereof. Preferably, the metal of the metal oxide is at least one metal contained in the Group 2, 3, 4, 13 and 14 elements of the Periodic Table of the Elements. Examples of such metals include magnesium, calcium, strontium, barium, yttrium, scandium, lanthanum, titanium, zirconium, hafnium, aluminum, gallium, indium, thalium, silicon, germanium, tin and lead. Titanium, zirconium, aluminum and silicon are preferred metals, with aluminum and silicon being more preferred. The metal oxide adsorbent used in this invention is also preferably impregnated to enhance oxygenate adsorption capacity. Any conventional impregnation method can be used. Examples of such methods are found in Gates, *Catalytic Chemistry*, pages 378-379, John Wiley & Sons, New York (1992). Preferred impregnated metal oxides include metal oxides containing at least one ion from Groups 2, 4, 6, 12, 13, 14, and 15 from the Periodic Table of the Elements; more preferably at least one ion from Groups 2 and 12. Particularly preferred ions include zinc and magnesium.

III. Description of Olefin Stream

The olefin stream from which the oxygenate is separated according to this invention can be provided from any conventional source. Such olefin streams include, for example, cracking of petroleum streams or catalytic reaction of oxygenates to form olefins.

This invention is particularly beneficial in removing oxygenate contaminants from olefin streams made in oxygenate to olefins processes. In these streams, oxygenate contaminants such as dimethyl ether or acetaldehyde can be present in relatively high concentrations, and the presence of such oxygenates can cause problems in further processing the olefins (particularly ethylene and/or propylene) from these streams. For example, these contaminants can poison many conventional polyethylene and polypropylene forming catalysts.

In one embodiment of the invention, the olefin stream from which the oxygenate is to be removed comprises not greater than about 1,000 wppm oxygenate; preferably not greater than about 500 wppm oxygenate; more preferably not greater than about 100 wppm dimethyl ether; and most preferably not greater than about 10 wppm oxygenate, based on total weight of the olefin stream. Of course, for oxygenate to be removed from the olefin stream, some measurable amount must be present. In one embodiment, the provided olefin stream will contain at least about 0.1 wppm oxygenate; and in another, at least about 1 wppm oxygenate, based on total weight of the olefin stream. Preferably, the oxygenate is dimethyl ether or acetaldehyde, more preferably dimethyl ether.

In another embodiment of the invention, the olefin stream contains ethylene, propylene, butylene, or a combination thereof. Desirably, the olefin stream contains at least about 50 wt % ethylene, propylene, butylene, or a combination thereof, based on total weight of the olefin stream. Preferably, the olefin stream contains from about 50 wt % to about 99 wt % ethylene, propylene, butylene, or a combination thereof; more preferably from about 55 wt % to about 99 wt % ethylene, propylene, butylene, or a combination thereof; and most preferably from about 60 wt % to about 95 wt % ethylene, propylene, butylene, or a combination thereof, based on total weight of the olefin stream.

In another embodiment, the olefin stream contains both ethylene and propylene. Desirably, the olefin stream contains at least about 50 wt % ethylene and propylene, based on total weight of the olefin stream. Preferably, the olefin stream contains from about 50 wt % to about 99 wt % ethylene and propylene; more preferably from about 55 wt % to about 99 wt % ethylene and propylene; and most preferably from about 60 wt % to about 95 wt % ethylene and propylene, based on total weight of the olefin stream.

In another embodiment, the olefin stream contains both propylene and butylene. Desirably, the olefin stream contains at least about 50 wt % propylene and butylene, based on total weight of the olefin stream. Preferably, the olefin stream contains from about 50 wt % to about 99 wt % propylene and butylene; more preferably from about 55 wt % to about 99 wt % propylene and butylene; and most preferably from about 60 wt % to about 95 wt % propylene and butylene, based on total weight of the olefin stream.

In another embodiment, the olefin stream that is provided comprises at least about 50 wt % ethylene, based on total weight of the olefin stream. Preferably, the provided olefin stream comprises at least about 75 wt % ethylene, and more preferably at least about 90 wt % ethylene, based on total weight of the olefin stream.

In another embodiment, the olefin stream that is provided also comprises at least about 50 wt % propylene, based on total weight of the olefin stream. Preferably, the provided olefin stream comprises at least about 75 wt % propylene, and more preferably 90 wt % propylene, based on total weight of the olefin stream.

The olefin stream optionally contains a relatively low concentration of ethane, propane, butane, or a combination thereof, preferably a lower concentration of ethane than propane. Preferably, the olefin stream comprises not greater than about 4 wt % ethane, more preferably not greater than about 3 wt % ethane, and most preferably not greater than about 2 wt % ethane, based on total weight of the olefin stream.

It is desirable that the olefin stream contain a relatively low concentration of propane. Preferably, the olefin stream comprises not greater than about 5 wt % propane, more preferably not greater than about 4 wt % propane, and most preferably not greater than about 3 wt % propane, based on total weight of the olefin stream.

It is also desirable that the provided olefin stream contain a relatively low concentration of butane. Preferably, the olefin stream comprises not greater than about 5 wt % butane, more preferably not greater than about 4 wt % butane, and most preferably not greater than about 3 wt % butane, based on total weight of the olefin stream.

It is desirable in this invention that the provided olefin stream contain not greater than about 1,000 wppm water, based on total weight of the olefin stream. Preferably the olefin stream contains not greater than about 500 wppm water, more preferably not greater than 100 wppm water, and most preferably not greater than about 10 wppm water, based on total weight of the olefin stream.

In another embodiment, the olefin stream that is provided comprises not greater than about 5 wt % $C_5+$ hydrocarbons, based on total weight of the olefin stream. According to this invention, $C_5+$ hydrocarbons refers to any hydrocarbon containing 5 or more carbons. Preferably the provided olefin stream comprises not greater than about 2 wt % $C_5+$ hydrocarbons, and more preferably not greater than about 1 wt % $C_5+$ hydrocarbons, based on total weight of the olefin stream.

This invention is particularly beneficial in removing oxygenate contaminants from olefin streams made in oxygenate to olefins processes. In oxygenate to olefins processes, an oxygenate is contacted with an olefin forming catalyst to form an olefin composition or stream.

In a preferred embodiment of the process of the invention, the oxygenate feedstock contains one or more oxygenates, more specifically, one or more organic compound(s) containing at least one oxygen atom. In a preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The feedstock, in one embodiment, contains one or more diluent(s), typically used to reduce the concentration of the feedstock, and are generally non-reactive to the feedstock or olefin forming catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent is either added directly to a feedstock entering into a reactor or added directly into a reactor, or added with an olefin forming catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

In one embodiment, the olefin forming catalyst is a molecular sieve capable of converting an oxygenate to an olefin compound. Such molecular sieves include zeolite as well as non-zeolite molecular sieves, and are of the large, medium or small pore type. Non-limiting examples of these molecular sieves capable of converting an oxygenate to an olefin compound are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves capable of converting an oxygenate to an olefin compound include ANA, BEA, CFI, CLO, DON, GIS, LTL, MER, MOR, MWW and SOD. Non-limiting examples of the preferred molecular sieves capable of converting an oxygenate to an olefin compound, include AEL, AFY, BEA, CHA, EDI, FAU, FER, GIS, LTA, LTL, MER, MFI, MOR, MTT, MWW, TAM and TON. In one preferred embodiment, the molecular sieve capable of converting an oxygenate to an olefin compound has an AEI topology or a CHA topology, or a combination thereof, most preferably a CHA topology.

The small, medium and large pore molecular sieves capable of converting an oxygenate to an olefin compound have from a 4-ring to a 12-ring or greater framework-type. In a preferred embodiment, the molecular sieves capable of converting an oxygenate to an olefin compound have 8-, 10- or 12-ring structures or larger and an average pore size in the range of from about 3 Å to 15 Å. In the most preferred embodiment, the molecular sieves capable of converting an oxygenate to an olefin compound, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves capable of converting an oxygenate to an olefin compound preferably have a molecular framework of one, preferably two or more corner-sharing [$TO_4$] tetrahedral units, more preferably, two or more [$SiO_4$], [$AlO_4$] and/or [$PO_4$] tetrahedral units, and most preferably [$SiO_4$], [$AlO_4$] and [$PO_4$] tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where E1 is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZNAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves capable of converting an oxygenate to an olefin compound include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves capable of converting an oxygenate to an olefin compound include aluminophosphate (ALPO) molecular sieves and silicoaluminophosphate (SAPO) molecular sieves and substituted, preferably metal substituted, ALPO and SAPO molecular sieves. The most preferred molecular sieves capable of converting an oxygenate to an olefin compound are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve capable of converting an oxygenate to an olefin compound, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_n)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves capable of converting an oxygenate to an olefin compound include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred molecular sieves capable of converting an oxygenate to an olefin compound include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve capable of converting an oxygenate to an olefin compound is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve capable of converting an oxygenate to an olefin compound comprises at least one intergrown phase of AEI and CHA frameworktypes. For example, SAPO-18, ALPO-18 and RUW-18 have an AEI framework-type, and SAPO-34 has a CHA framework-type.

In one embodiment, the molecular sieves capable of converting an oxygenate to an olefin compound are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

The molecular sieves capable of converting an oxygenate to an olefin compound are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in GM. Wolterman, et al., Stud. Surf. Sci. and Catal., 76, pages 105-144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve capable of converting an oxygenate to an olefin compound, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

In another embodiment, the formulated molecular sieve catalyst composition capable of converting an oxygenate to an olefin compound contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition capable of converting an oxygenate to an olefin compound, based on the total weight of the binder, molecular sieve, and matrix material, is from about 2% by weight to about 30% by weight, preferably from about 5% by weight to about 20% by weight, and more preferably from about 7% by weight to about 15% by weight.

Once the molecular sieve catalyst composition capable of converting an oxygenate to an olefin compound is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

The process for converting a feedstock, especially a feedstock containing one or more oxygenates, in the presence of a molecular sieve catalyst composition capable of converting an oxygenate to an olefin compound, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred oxygenate conversion reactor types are riser reactors, such as those generally described in Riser Reactor, *Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which references are all herein fully incorporated by reference.

In the preferred embodiment, a fluidized bed process or high velocity fluidized bed process includes a reactor system, a regeneration system and a recovery system. The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1,000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, is not critical. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV in the oxygenate conversion reactor ranges from about 1 $hr^{-1}$ to about 5000 $hr^{-1}$, preferably from about 2 $hr^{-1}$ to about 3000 $hr^{-1}$ $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the oxygenate conversion reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the processes for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is a Group IIIA or VIII element from the Periodic Table of Elements) molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

According to one embodiment, the conversion of the primary oxygenate, e.g., methanol, is from about 90 wt % to about 98 wt %, based on the total amount of the primary oxygenate being converted. According to another embodiment the conversion of methanol is from about 92 wt % to about 98 wt %, preferably from about 94 wt % to about 98 wt %, based on the total amount of the primary oxygenate being converted.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

The oxygenate to olefin process forms a substantial amount of water as a by-product. Much of this water can be removed by cooling the olefin stream from the oxygenate reactor to a temperature below the condensation temperature of the water in the stream. Preferably, the temperature of the product stream is cooled to a temperature below the condensation temperature of the oxygenate feed for the oxygenate to olefins process. In certain embodiments, it is desirable to cool the product stream below the condensation temperature of methanol.

A quench column is one type of equipment that is effective in cooling the olefin stream from the olefin to oxygenate reaction process. In a quench column, a quenching fluid is directly contacted with the olefin stream to cool the stream to the desired condensation temperature. Condensation produces the condensed water containing stream, which is also referred to as a heavy bottoms stream. The olefin portion of the olefin product stream remains a vapor, and exits the quench column as an overhead vapor stream. The overhead vapor stream is rich in olefin product, and can also contain some oxygenated hydrocarbon by-products as well as water.

In one embodiment, the quenching fluid is a recycle stream of the condensed water containing, heavy bottoms stream of the quench column. This water containing stream is desirably cooled, e.g., by a heat exchanger, and injected back into the quench column. It is preferred in this embodiment to not inject cooling medium from an outside source into the quench column, although it may be desirable to do so in other separation equipment down stream of the quench column.

In one particular embodiment of the invention, the quenched olefin stream is further processed by compression, preferably multi-staged compression. Two, three, four or more stages can be used, with two or three stages being preferred.

In another embodiment of the invention, the olefin stream is compressed to a pressure that is greater than that at which the oxygenate to olefin reaction process is carried out. Preferably, the olefin stream is compressed to a pressure of at least about 30 psia (207 kPa), more preferably at least about 50 psia (345 kPa), most preferably at least about 100 psia (689 kPa). High pressure ranges are particularly preferred, with the upper limit being a practical one based on cost of design and ease of operation. Practical high pressure limits are generally considered to be up to about 5,000 psia (34,450 kPa), with lower limits of about 1,000 psia (6,895 kPa), about 750 psia (5171 kPa), and about 500 psia (3447 kPa) being increasingly preferred.

In one embodiment of the invention, the provided olefin stream is quenched, compressed, and separated into various olefin component streams. The olefin component streams include ethylene and/or propylene containing streams, such as those described above. The olefin component streams are then contacted with the solid dimethyl ether removing agent of the invention to remove a majority (i.e., greater than 50%) of the dimethyl ether from the olefin stream.

IV. Description of Oxygenate Removal Process

In this invention, removal or adsorption of the oxygenate from the olefin stream is accomplished using one or more adsorption beds. The beds can be arranged in series or parallel, and can be any type of conventional bed system.

The adsorption beds can be operated at ambient temperature or at elevated temperature as required. Flow of the olefin stream through the beds can be either upward or downward. The adsorption process can be carried out either in the gas phase or the liquid phase.

The temperature at which the provided olefin stream is contacted with the solid adsorbent can vary over a wide range. In one embodiment, the provided olefin stream is contacted with the solid adsorbent at a temperature of from about 0° C. to about 600° C. In another embodiment, the provided olefin stream is contacted with the solid adsorbent in the gas phase at a temperature of from about 20° C. to about 600° C. In yet another embodiment, the provided olefin stream is contacted with the solid adsorbent in the liquid phase at a temperature of from about 0° C. to about 85° C.

The pressure at which the provided olefin stream is contacted with the solid adsorbent can also vary over a wide range. In one embodiment, the provided olefin stream is contacted with the solid adsorbent at a pressure of from about 0.01 psig to about 600 psig.

Space velocity at which the provided olefin stream is contacted with the solid adsorbent can vary widely and designation of particular space velocities depends on whether the contact is in the gas or liquid phase. For example, in one embodiment in the gas phase, the provided olefin stream is contacted with the solid adsorbent at a gas hourly space velocity (GHSV) of from about 100 $hr^{-1}$ to about 20,000 $hr^{-1}$. In another example in the liquid phase, the provided olefin stream is contacted with the solid adsorbent at a liquid hourly space velocity (LHSV) of from about 0.01 $hr^{-1}$ to about 100 $hr^{-1}$.

In one embodiment of the invention, a majority of the oxygenate present in the provided olefin stream is removed from the olefin stream. In another embodiment, at least about 75% of the oxygenate present in the provided olefin stream is removed from the olefin stream. Preferably, at least about 85% of the oxygenate in the provided olefin stream is removed, more preferably at least about 95% is removed, and most preferably at least about 99% is removed. Preferably the oxygenate removed is dimethyl ether or acetaldehyde, more preferably dimethyl ether.

V. Regeneration of Solid Adsorbent

Regeneration of the solid adsorbent can be carried out by any conventional method. Such methods include treatment with a stream of a dry inert gas such as nitrogen at elevated temperature.

In one embodiment of the invention, the solid adsorbent is regenerated following contacting with the provided olefin stream. In this embodiment, it is preferable to regenerate the solid adsorbent before the adsorbent reaches full adsorption capacity. That is, it is preferred to regenerate the solid adsorbent just before it becomes fully saturated. At full saturation, breakthrough of the oxygenate occurs, meaning that oxygenate is no longer adsorbed from the olefin stream, and that the adsorbent is essentially ineffective in operation.

The temperature at which regeneration takes place is one at which the oxygenate is effectively removed from within the pore structure of the sieve, preferably at a temperature at which the oxygenate is evaporated. In one embodiment of the invention, the solid adsorbent is regenerated at a temperature of from about 200° C. to about 500° C.

The pressure at which the regeneration takes place is also favorable for effective removal of oxygenate, preferably at a temperature at which the oxygenate is evaporated from the pore structure of the adsorbent, particularly from the pore structure of a molecular sieve adsorbent. In one embodiment, the solid adsorbent is regenerated at a pressure of from about 0.01 psig to about 400 psig.

In one embodiment of the invention, an inert medium is used to sweep the adsorbent during the regeneration process to aid in removing the oxygenate within the pore structure. In this embodiment, gas hourly space velocity (GHSV) during regeneration is not critical and can vary widely. In one embodiment, the solid adsorbent is regenerated at a gas hourly space velocity of from 10 $hr^{-1}$ to 5,000 $hr^{-1}$.

VI. Use of Olefin Product

The ethylene and/or propylene streams treated according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene and/or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_4+$ olefins, particularly butylene, treated according to this invention. The olefins treated according to this invention can also be used in the manufacture of such compounds as aldehydes, acids such as $C_2$-$C_{13}$ mono carboxylic acids, alcohols such as $C_2$-$C_{12}$ mono alcohols, esters made from the $C_2$-$C_{12}$ mono carboxylic acids and the $C_2$-$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4+$ olefins, butylene in particular, are particularly suited for the manufacture of aldehydes, acids, alcohols, esters made from $C_5$-$C_{13}$ mono carboxylic acids and $C_5$-$C_{13}$ mono alcohols and linear alpha olefins.

VII. Examples of Oxygenate Removal

An embodiment of this invention is exemplified in the following non-limiting Examples:

EXAMPLE 1

Invention; Zn—X Zeolite 39.5 g of Na—X zeolite (obtained from Union Carbide Corporation) were packed into a column for ion exchange. The column was heated to 65° C., and ultra high purity water was pumped through the column. An ion-exchange solution was prepared by adding 30 g of anhydrous zinc chloride (ALFA Products) to 700 ml ultra high purity water, followed by filtering to obtain a clear solution. This solution was then pumped through the Na—X zeolite at a rate of approximately 4-5 ml/min. Filtered, ultra high purity water was then passed over the column until a negative silver nitrate test was obtained, thereby forming a Zn—X zeolite. The Zn—X zeolite was recovered and dried at 110° C. for 3 hours under air flow, then calcined at 400° C. for 10 hours.

The calcined Zn—X zeolite was subjected to continuous dimethyl ether (DME) adsorption testing as follows. Four grams of the Zn—X zeolite were pressed and sieved to 20×40 mesh size, mixed with SiC of approximately the same mesh size, and the mixture charged to a reactor. The mixture was dried under an approximately 500 $hr^{-1}$ GHSV flow of He at 200° C. for 4 hours, and then cooled to 28° C. Propylene feed containing approximately 20 mppm DME was then contacted with the adsorbent by flowing across the adsorbent zeolite at a flowrate of 3 hr$^{-1}$ LHSV and a pressure of 380 psig (2721 kPa). After approximately 360 hours, the level of DME in the propylene feed was decreased to approximately 6 mppm for a period of approximately 100 hours, then increased back to the original level of 20 mppm for the remainder of the test.

The amount of DME in the feed, the amount of DME in the effluent, the amount of DME adsorbed by the zeolite, and the amount of propylene oligomers formed as a result of contacting the DME with the zeolite, were measured as a function of time on stream (TOS). The results are shown in the FIGURE. The FIGURE shows that DME breakthrough occurs after 700 hours on stream, at which point the weight percent loading of DME with respect to the Zn—X zeolite is 1.41 wt %. No DME is observed in the effluent when the feed level is decreased to 6 mppm, indicating a strong adsorption of DME to the adsorbent at low levels of DME.

The FIGURE further shows that the oligomer level in the product stream decreases from an initial value of approximately 1.1 mol % (11,000 mppm) to a final value of around 600 wppm. The cumulative oligomer selectivity (total amount of oligomer formed with respect to total amount of propylene contacted with the adsorbent) was calculated to be 0.54 wt %. The DME adsorption capacity, oligomer level in the propylene effluent, and cumulative oligomer selectivity are also summarized in the Table.

EXAMPLE 2

Comparative; K—X Zeolite

A precursor solution was prepared by adding 74 g of potassium chloride (KCl) to 500 ml of deionized water to form a 2M KCl solution. 200 ml of the solution was added to 20 g of Na—X zeolite (Union Carbide Corporation) in a 500 ml glass bottle. The bottle was capped and periodically mixed over a period of 4 hr. The solution was then decanted and an additional 200 ml of the original ion-exchange solution was added to the bottle. The bottle was again periodically mixed over a period of 4 hr, and allowed to sit overnight. The next day, the solution was decanted and the solid was washed 5 times, each time by adding 200 ml of deionized water, mixing, and decanting the solution. The solid was then dried for 2 hr at 110° C. and calcined at 500° C. in air for 4 hr, thereby forming a K—X zeolite.

The K—X zeolite was subjected to continuous DME adsorption testing as in Example 1. The DME adsorption capacity, oligomer level in the propylene effluent, and cumulative oligomer selectivity were determined, and are summarized in the Table.

EXAMPLE 3

Comparative; K—Y Zeolite

K—Y zeolite was obtained from Davison Chemical, and subjected to continuous DME adsorption testing as in Example 1. The DME adsorption capacity, oligomer level in the propylene effluent, and cumulative oligomer selectivity were determined, and are summarized in the Table.

TABLE

Results from Continuous DME Adsorption Testing

| Adsorbent | DME adsorption capacity (wt %) | Oligomer level in effluent propylene (mppm) | Cumulative oligomer selectivity (overall wt % produced) |
|---|---|---|---|
| Zn-X zeolite | 1.41 | 700-11,000 | 0.54 |
| K-X zeolite | 0.03 | 100-200 | 0.11 |
| K-Y zeolite | 0.04 | 109-878 | 0.05 |

The FIGURE and Table illustrate that Zn—X zeolite provides a relatively high DME adsorption capacity in a continuous process. In addition, the results also show that the Zn—X zeolite has a relatively low activity in converting propylene to oligomers in this continuous test. The amount of oligomers present in the effluent propylene in this test is below approximately 1 wt % for the majority of the test, leading to an overall oligomer selectivity of 0.54 wt %, with respect to the total amount of propylene contacted with the Zn—X zeolite.

Having now fully described this invention, it will be appreciated by those skilled in the art that the invention can be performed within a wide range of parameters within what is claimed, without departing from the spirit and scope of the invention.

What is claimed is:

1. A process for forming a polyolefin, the process comprising the steps of:
   i) providing an oxygenate stream for conversion to olefins;
   ii) removing at least a portion of the oxygenate from the olefin stream to form a reduced-oxygenate olefin stream by the following steps:
      a) providing an olefin stream, wherein the olefin stream contains oxygenate, and the olefin stream is comprised of greater than 50 wt % ethylene and propylene, and wherein the olefin stream comprises not greater than 5 wt % butane; and
      b) contacting the provided olefin stream with a solid adsorbent to remove oxygenate from the provided olefin stream, wherein the solid adsorbent has an oxygenate adsorption capacity of at least 0.1 wt % and a cumulative oligomer selectivity of not greater than 5 wt %, wherein the solid adsorbent comprises at least one ion from Group 2, 4, 6, 12, 13, 14 or 15 of the Periodic Table of the Elements; and
   iii) polymerizing one or more olefins in the reduced-oxygenate olefin stream, optionally in conjunction with one or more olefins from a source other than the olefin stream, in the presence of a polyolefin-forming catalyst under conditions sufficient to form a polyolefin.

2. The process of claim 1, wherein the solid adsorbent has an oxygenate adsorption capacity of at least 0.2 wt %.

3. The process of claim 2, wherein the solid adsorbent has an oxygenate adsorption capacity of at least 0.5 wt %.

4. The process of claim 3, wherein the solid adsorbent has an oxygenate adsorption capacity of at least 1.0 wt %.

5. The process of claim 1, wherein the solid adsorbent has a cumulative oligomer selectivity of not greater than 3 wt %.

6. The process of claim 5, wherein the solid adsorbent has a cumulative oligomer selectivity of not greater than 2 wt %.

7. The process of claim 6, wherein the solid adsorbent has a cumulative oligomer selectivity of not greater than 1 wt %.

8. The process of claim 1, wherein the contacting removes a majority of the oxygenate from the provided olefin stream.

9. The process of claim 8, wherein the oxygenate in the provided olefin stream is dimethyl ether or acetaldehyde.

10. The process of claim 9, wherein the oxygenate in the provided olefin stream is dimethyl ether.

11. The process of claim 1, wherein the solid adsorbent comprises at least one ion from Group 2 or 12 of the Periodic Table of the Elements.

12. The process of claim 11, wherein the solid adsorbent comprises magnesium or zinc.

13. The process of claim 1, wherein the provided olefin stream comprises at least 50 wt % propylene and butylene, based on total weight of the provided olefin stream.

14. The process of claim 1, wherein the provided olefin stream comprises not greater than 1,000 wppm oxygenate, based on total weight of the provided olefin stream.

15. The process of claim 14, wherein the oxygenate is dimethyl ether or acetaldehyde.

16. The process of claim 15, wherein the oxygenate is dimethyl ether.

17. The process of claim 1, wherein the solid adsorbent is a molecular sieve or metal oxide.

18. The process of claim 1, wherein the solid adsorbent is a crystalline molecular sieve.

19. The process of claim 17, wherein the solid adsorbent is a molecular sieve selected from the group consisting of silicates, aluminosilicates, aluminophosphates, and silicoaluminophosphates.

20. The process of claim 1, wherein the solid adsorbent is a molecular sieve having a framework structure of at least 8 rings.

21. The process of claim 20, wherein the molecular sieve is a zeolite.

22. The process of claim 20, wherein the molecular sieve is zeolite X, zeolite Y, ZSM-5, ZSM-11, ZSM-14, ZSM-17, ZSM-18, ZSM-20, ZSM-31, ZSM-34, ZSM-41 or ZSM-46.

23. The process of claim 20, wherein the molecular sieve is zeolite X or Y.

24. The process of claim 20, wherein the molecular sieve is zeolite X.

25. The process of claim 1, wherein the solid adsorbent is regenerated following contacting with the provided olefin stream.

26. A process for forming a polyolefin, the process comprising the steps of:
  i) providing an oxygenate composition containing dimethyl ether for conversion to olefins;
  ii) removing at least a portion of the dimethyl ether from the olefin stream to form a reduced-oxygenate olefin stream by the following steps:
    a) contacting an oxygenate with a molecular sieve catalyst to form an olefin composition, wherein the olefin composition contains greater than 50 wt % ethylene and propylene and contains dimethyl ether, and wherein the olefin composition comprises not greater than 5 wt % butane; and
    b) contacting at least a portion of the olefin composition containing the dimethyl ether with a solid adsorbent to remove at least a portion of the dimethyl ether from the provided olefin stream, wherein the solid adsorbent has a dimethyl ether adsorption capacity of at least 0.1 wt % and a cumulative oligomer selectivity of not greater than 5 wt %, wherein the solid adsorbent comprises at least one ion from Group 2, 4, 6, 12, 13, 14 or 15 of the Periodic Table of the Elements and
  iii) polymerizing one or more olefins in the reduced-oxygenate olefin stream, optionally in conjunction with one or more olefins from a source other than the olefin stream, in the presence of a polyolefin-forming catalyst under conditions sufficient to form a polyolefin.

27. The process of claim 26, wherein the solid adsorbent has a dimethyl ether adsorption capacity of at least 0.2 wt %.

28. The process of claim 27, wherein the solid adsorbent has a dimethyl ether adsorption capacity of at least 0.5 wt %.

29. The process of claim 28, wherein the solid adsorbent has a dimethyl ether adsorption capacity of at least 1.0 wt %.

30. The process of claim 26, wherein the solid adsorbent has a cumulative oligomer selectivity of not greater than 3 wt %.

31. The process of claim 30, wherein the solid adsorbent has a cumulative oligomer selectivity of not greater than 2 wt %.

32. The process of claim 26, wherein the contacting removes a majority of the dimethyl ether from the provided olefin stream.

33. The process of claim 26, wherein the solid adsorbent comprises at least one ion from Group 2 or 12 of the Periodic Table of the Elements.

34. The process of claim 33, wherein the solid adsorbent comprises magnesium or zinc.

35. The process of claim 26, wherein the olefin composition formed in step a) is further processed to remove non-olefin components from the olefin composition prior to contacting the olefin composition with the solid adsorbent in step b).

36. The process of claim 26, wherein the olefin composition formed in step a) is further processed prior to carrying out step b).

37. The process of claim 26, wherein the olefin composition formed in step a) is dewatered and split into at least two olefin streams, and one of the olefin streams is the olefin stream of step b).

38. The process of claim 26, wherein the solid adsorbent that removes at least a portion of the dimethyl ether from the olefin stream is a molecular sieve or metal oxide.

39. The process of claim 38, wherein the solid adsorbent that removes at least a portion of the dimethyl ether from the olefin stream is a crystalline molecular sieve.

40. The process of claim 38, wherein the solid adsorbent is a molecular sieve is selected from the group consisting of silicates, aluminosilicates, aluminophosphates, and silicoaluminophosphates.

41. The process of claim 38, wherein the solid adsorbent is a molecular sieve having a framework structure of at least 8 rings.

42. The process of claim 41, wherein the molecular sieve is a zeolite.

43. The process of claim 41, wherein the molecular sieve is zeolite X, zeolite Y, ZSM-5, ZSM-11, ZSM-14, ZSM-17, ZSM-18, ZSM-20, ZSM-31, ZSM-34, ZSM-41 or ZSM-46.

44. The process of claim 42, wherein the molecular sieve is zeolite X or Y.

45. The process of claim 44, wherein the molecular sieve is zeolite X.

46. The process of claim 26, wherein the olefin composition of step b) comprises at least 50 wt % ethylene, propylene, butylene, or a combination thereof, based on total weight of the olefin composition of step b).

47. The process of claim 26, wherein the provided olefin stream comprises not greater than 1,000 wppm dimethyl ether, based on total weight of the provided olefin stream.

48. The process of claim 30, wherein the solid adsorbent is regenerated following contacting with the provided olefin stream.

49. A process for removing dimethyl ether from an olefin stream, the process comprising the steps of:
  a) providing an olefin stream, wherein the olefin stream comprises dimethyl ether and greater than 50 wt % ethylene, propylene, or a combination thereof, based on total weight of the olefin stream, and wherein the olefin stream comprises not greater than 5 wt % butane; and
  b) contacting the provided olefin stream with a molecular sieve to remove at least a portion of the dimethyl ether from the provided olefin stream, wherein the molecular sieve has a dimethyl ether adsorption capacity of at least 0.1 wt % and an oligomer accumulation of not greater than 5 wt %, wherein the molecular sieve comprises at least one ion from Group 2, 4, 6, 12, 13, 14 or 15 of the Periodic Table of the Elements.

50. The process of claim 49, wherein the molecular sieve has a dimethyl ether adsorption capacity of at least 0.2 wt %.

51. The process of claim 50, wherein the molecular sieve has a dimethyl ether adsorption capacity of at least 0.5 wt %.

52. The process of claim 51, wherein the molecular sieve has a dimethyl ether adsorption capacity of at least 1.0 wt %.

53. The process of claim 49, wherein the molecular sieve has a cumulative oligomer selectivity of not greater than 3 wt %.

54. The process of claim 53, wherein the molecular sieve has a cumulative oligomer selectivity of not greater than 2 wt %.

55. The process of claim 54, wherein the molecular sieve has a cumulative oligomer selectivity of not greater than 1 wt %.

56. The process of claim 49, wherein the contacting removes a majority of the dimethyl ether from the provided olefin stream.

57. The process of claim 49, wherein the molecular sieve comprises at least one ion from Group 2 or 12 of the Periodic Table of the Elements.

58. The process of claim 57, wherein the molecular sieve comprises magnesium or zinc.

59. The process of claim 49, wherein the provided olefin stream comprises at least 50 wt % propylene and butylene, based on total weight of the provided olefin stream.

60. The process of claim 49, wherein the molecular sieve is a crystalline molecular sieve.

61. The process of claim 60, wherein the molecular sieve is selected from the group consisting of silicates, aluminosilicates, aluminophosphates, and silicoaluminophosphates.

62. The process of claim 60, wherein the molecular sieve has a framework structure of at least 8 rings.

63. The process of claim 60, wherein the molecular sieve is a zeolite.

64. The process of claim 60, wherein the molecular sieve is zeolite X, zeolite Y, ZSM-5, ZSM-11, ZSM-14, ZSM-17, ZSM-18, ZSM-20, ZSM-31, ZSM-34, ZSM-41 or ZSM-46.

65. The process of claim 60, wherein the molecular sieve is zeolite X or Y.

66. The process of claim 65, wherein the molecular sieve is zeolite X.

67. The process of claim 1, wherein the olefin stream is comprised of about 55 wt % to about 99 wt % of ethylene and propylene.

68. The process of claim 26, wherein the olefin composition contains about 55 wt % to about 99 wt % of ethylene and propylene.

69. The process of claim 49, wherein the olefin stream comprises about 55 wt % to about 99 wt % of ethylene, propylene, or a combination thereof.

70. The process of claim 1, wherein the olefin stream is comprised of about 60 wt % to about 95 wt % of ethylene and propylene.

71. The process of claim 26, wherein the olefin composition contains about 60 wt % to about 95 wt % of ethylene and propylene.

72. The process of claim 49, wherein the olefin stream comprises about 60 wt % to about 95 wt % of ethylene, propylene, or a combination thereof.

* * * * *